United States Patent [19]
Seko et al.

[11] Patent Number: 5,902,905
[45] Date of Patent: May 11, 1999

[54] METHOD FOR PRODUCING ARYLVINYLSULFONE

[75] Inventors: Shinzo Seko, Toyonaka; Akio Kurihara, Ibaraki; Isao Kurimoto, Suita, all of Japan

[73] Assignee: Sumitomo Chemical Company, Limited, Osaka, Japan

[21] Appl. No.: 08/968,306

[22] Filed: Nov. 12, 1997

[30] Foreign Application Priority Data

Nov. 12, 1996 [JP] Japan .................................. 8-300204
Jan. 18, 1997 [JP] Japan .................................. 9-001232

[51] Int. Cl.$^6$ .............................................. C07C 315/04
[52] U.S. Cl. ............................................. 568/28; 568/36
[58] Field of Search ......................... 568/28, 36

[56] References Cited

U.S. PATENT DOCUMENTS

| | | |
|---|---|---|
| 2,554,576 | 5/1951 | Landau . |
| 2,801,267 | 7/1957 | Young . |
| 3,242,041 | 3/1966 | Aichenegg . |
| 4,386,221 | 5/1983 | Hyatt ........................................ 568/28 |
| 4,855,411 | 8/1989 | Thompson et al. . |

FOREIGN PATENT DOCUMENTS

| | | |
|---|---|---|
| 0058370 | 8/1982 | European Pat. Off. . |
| 0352682 | 1/1990 | European Pat. Off. . |
| 6.099M | 7/1968 | France . |
| 842198 | 6/1952 | Germany . |
| 877067 | 7/1953 | Germany . |
| 3904591 | 8/1990 | Germany . |
| 3941810 | 6/1991 | Germany . |
| 4001315 | 7/1991 | Germany . |

OTHER PUBLICATIONS

CA 113 171590 Org Prep Proced Int 22(4) 522–5 Shimizugawa, 1990.
Horner et al., "Fluoreszierende und nicht fluoreszierende (Aryl)(vinyl)sulfone–Reagenzien zum Schutz und Nachweis von Thiolfunktionen", Liebigs Ann. Chem., 1985, pp. 22–33.
Shimizu, et al., "Regioselectivity of 1,3–Dipolar Cycloaddition Reactions of Nitrilimines with Aryl Vinyl Sulfones", J. Org. Chem., 1985, vol. 50, No. 6, pp. 904–907.
"Synthesis of Arylvinylsulfones and its reactivity", Kogyou Kagku Zasshi 62, 1959, pp. 825–828.
Horner et al., "Aryl–Vinylsulfone–Reagentien Zum Schutz und Nachweis Von Thiolfunktionen", Phosphorous and Sulfter, 1983, vol. 15, pp. 1–8.
Boudet–Dalbin, et al., "Composes a groupe trimethoxyphenylsulfonyle", Eur. J. Med. Chem.—Chim. Ther., 1986, vol. 21, No. 2, pp. 131–137.
Marshall, et al., "Elimination and Addition Reactions. Part 32.$^1$ Discrimination between Concerted and Stepwise Processes in Activated Elimination Reactional", J.C.S Perkin II 1977, pp. 1914–1919.
Klamann et al., "Darstellung und Eigenschaften einiger β–Oxyathyl– und β–Chlorathyl–Verbindungen", Chem. Ber., 1955, vol. 88, pp. 201–205.
Naghipur et al., "Formation of Benzoxathiete under Mild Conditions and Its Valence Tautomerism in Solution to Monothio–o–benzoquinone: An Experimental and Quantum Chemical Study", 1989, vol. 111, pp. 258–268. (Search Report included).
J. Org. Chem. 1983, 48, 4978–4986.
J. Chem. Soc. 1754 (1949).
Org. Syn 64, 157 (1985) pp. 453–456.
J. Chem. Soc. Chem. Commun., 1984, 486–488.
Synthetic communications, 26(2), 211–216 (1996).
J. Org. Chem. 1993, 58, 4506–4508.
Bull. Korean Chem. Soc. 1995, vol. 16, No. 7 pp. 670–672.

*Primary Examiner*—Gary Geist
*Assistant Examiner*—Jean F Vollano
*Attorney, Agent, or Firm*—Pillsbury Madison & Sutro LLP

[57] ABSTRACT

There is provided a method for producing arylvinylsulfone of the formula:

[I]

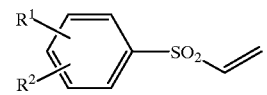

wherein, $R^1$ and $R^2$ denote each independently a hydrogen atom,
a halogen atom, a lower alkyl group, a lower alkoxy group,
a nitro group, an amino group, a lower alkylamino group and
a lower di(alkylamino) group,
which comprises reacting β-haloethylarylsulfone of the formula:

[II]

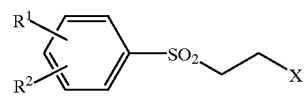

wherein, $R^1$ and $R^2$ are as defined above and X denotes a halogen atom, with an alkali metal carbonate or an alkali metal hydrogencarbonate in the presence of a catalytic amount of an amine or its inorganic acid salt or a quaternary ammonium salt.

19 Claims, No Drawings

METHOD FOR PRODUCING ARYLVINYLSULFONE

BACKGROUND OF THE INVENTION

1. Field of the Invention

The present invention relates to a method for producing arylvinylsulfone.

2. Description of the Related Art

Vinylsolfone is widely used as an important functional group and has been prepared, for example, by reacting β-chloroethylphenylsulfone with a stoichiometric amount of sodium hydroxide or triethylamine. [U.S. Pat. No. 2,554, 576, DE 877607, J. Org. Chem., 58, 4506 (1993) and J. Chem. Soc., 1754 (1949)]

Alternatively, a readily available 2-phenylsulfonylethanol is mesylated and then the mesylate is reacted with triethylamine [Bull. Korean Chem. Soc., 16, 670 (1995)].

These processes were not always satisfactory, however, in that the yield of the desired product was not satisfactory when sodium hydroxide was used or a further tedious process was required to cope with a large amount of used triethylamine in wastewater, or the expensive mesyl chloride was required.

Therefore, a further method to provide arylvinylsulfone has been desired.

SUMMARY OF THE INVENTION

The present inventors have found a novel process for producing arylvinylsulfone, which comprises reacting β-haloethylarylsulfone with an alkali metal carbonate or an alkali metal hydrogencarbonate or a mixture thereof in the presence of a catalytic amount of an amine or its inorganic salt or a quaternary ammonium salt, and also found a process which comprises reacting a chlorinating agent with 2-arylsulfonylethanol to produce β-haloethylarylsulfone, whereby reducing the burden of treating used triethylamine and producing the desired compound in good yield and economically.

The present invention provides:

a method for producing arylvinylsulfone of the formula:

[I]

$$\text{R}^1\text{-Ar-SO}_2\text{-CH=CH}_2$$

wherein, $R^1$ and $R^2$ indicate each independently a hydrogen atom, a halogen atom, a lower alkyl group, a lower alkoxy group, a nitro group, an amino group, a lower alkylamino group and a lower di(alkyl)amino group, which comprises: reacting β-haloethylarylsulfone of the formula:

[II]

$$\text{R}^1\text{-Ar-SO}_2\text{-CH}_2\text{CH}_2\text{-X}$$

wherein, $R^1$ and $R^2$ are as de-fined above and X denotes a halogen atom, with an alkali metal carbonate or an alkali metal hydrogencarbonate or a mixture thereof in the presence of a catalytic amount of an amine or its inorganic acid salt or a quaternary ammonium salt; and a method for producing β-haloethylarylsulfone of the formula [II] as defined above, which comprises reacting 2-arylsulfonylethanol of the formula:

[III]

$$\text{R}^1\text{-Ar-SO}_2\text{-CH}_2\text{CH}_2\text{-OH}$$

wherein, $R^1$ and $R^2$ are as defined above, with a chlorinating agent.

DESCRIPTION OF THE PREFERRED EMBODIMENTS

First, a description will be made to the method for producing arylvinylsulfone of the formula [I] as defined above, which comprises reacting β-haloethylarylsulfone of the formula [II] as defined above with an alkali metal carbonate or an alkali metal hydrogencarbonate or a mixture thereof in the presence of a catalytic amount of an amine or its inorganic acid salt or a quaternary ammonium salt.

In the β-haloethylarylsulfone of the formula [II], the halogen atom represented by $R^1$ or $R^2$ includes a fluorine, chlorine, bromine and iodine atom Examples of the lower alkyl group for $R^1$ or $R^2$ include a straight or branched chain alkyl group having 1 to 6 carbon atoms such as a methyl group, an ethyl group, a n-propyl group, a n-butyl group, a n-pentyl group, an i-propyl group, an i-butyl group, a sec-butyl group, a t-butyl group, a neopentyl group, a n-hexyl group and the like.

Examples of the lower alkoxy group for $R^1$ or $R^2$ include a straight or branched chain alkoxy group having 1 to 6 carbon atoms such as a methoxy group, an ethoxy group, an n-propoxy group, an n-butoxy group, an n-pentoxy group, an i-propoxy group, an i-butoxy group, a sec-butoxy group, a t-butoxy group, an neopentoxy group, a n-hexyloxy group and the like.

The lower alkylamino group for $R^1$ and $R^2$ includes an amino group substituted by one lower alkyl group, wherein the lower alkyl group here includes the alkyl groups as defined for $R^1$ and $R^2$ above.

Examples of the lower alkylamino group include a methylamino group, an ethylamino group, a t-butylamino group and the like.

The lower di(alkyl)amino group for $R^1$ and $R^2$ includes an amino group substituted by two lower alkyl groups, wherein the lower alkyl group is the same alkyl groups as described above.

Examples of the lower di(alkyl)amino groups include a dimethylamino group, a methylethylamino group, a diethylamino group, a t-butylmethylamino group and the like.

Examples of the halogen atom represented by X include a chlorine atom, bromine atom, iodine atom and the like.

Specific examples of the β-haloethylarylsulfone of the formula [II] include (βchloroethylsulfonyl)benzene, 4-chloro-1-(β-chloroethylsulfonyl)benzene, 1-(β-chloroethylsulfonyl)-3,4-dichlorobenzene, 4-bromo-1-(β-chloroethylsulfonyl)benzene, 1-(β-chloroethylsulfonyl)-4-fluorobenzene, 1-(β-chloroethylsulfonyl)-4-iodobenzene, 1-(β-chloroethylsulfonyl)-4-methylbenzene, 1-(β-chloroethylsulfonyl)-2,4-dimethylbenzene, 1-(β-chloroethylsulfonyl)-4-ethylbenze, 1-(β-chloroethylsulfonyl)-4-i-butylbenzene, 1-(β-chloroethylsulfonyl)-4-t-butylbenzene, 1-(β-chloroethylsulfonyl)-4-methoxybenzene, 1-(β-chloroethylsulfonyl)-3,4-dimethoxybenzene, 1-(β-chloroethylsulfonyl)-4-t-butoxybenzene, 3-(β- chloroethylsulfonyl)-aniline, 3-(β-chloroethylsulfonyl)-N-methylaniline 3-(β-chloroethylsulfonyl)-N-ethylaniline, 3-(β-chloroethylsulfonyl)-N,N-dimethylaniline, 3-(β-chloroethylsulfonyl)-N,N-diethylaniline, 1-(β-chloroethylsulfonyl)-3-nitrobenzene, and compounds having a β-bromoethylsulfonyl group or a β-iodoethylsulfonyl group in place of the β-chloroethylsulfonyl group in the above-described compound.

The alkali metal carbonate, for example, includes potassium carbonate, sodium carbonate and the like, and the alkali metal hydrogencarbonate, for example, includes potassium hydrogencarbonate, sodium hydrogencarbonate and the like. The alkali metal or alkali metal hydrogen carbonate may be used alone or in combination thereof, and among them, potassium carbonate is preferably used.

The amount of the alkali metal carbonate or alkali metal hydrogencarbonate to be used is usually not less than 0.8 mol, preferably from 1 to 4 moles in terms of alkali metal per mol of β-haloethylarylsulfone.

Though the alkali metal carbonate or alkali metal hydrogencarbonate can be used in the form of powder, it is preferably used in the form of an aqueous solution, of which concentration can be appropriately set according to the alkali metal carbonate or alkali metal hydrogen carbonate employed.

The amine or its inorganic acid salt or a quaternary ammonium salt may be used alone or in combination-thereof.

The amine includes ammonia (e.g., aqueous ammonia), a heteroaryl amine, a primary, secondary or tertiary amine or its inorganic acid salt and is commercially available or may be obtained by a conventional method. The secondary or tertiary amine or its inorganic acid salt or a quaternary ammonium salt is preferably used in the present invention.

Examples of the heteroaryl amine include pyridine, 2-picoline, 3-picoline, 4-picoline and 2,4-dimethylpyridine.

The primary amine includes an amine compound of the formula: $QNH_2$, wherein

Q represents:
  a saturated or unsaturated hydrocarbon group which may substituted, or
  an aryl group which may be substituted.

The secondary amine includes an amine compound of the formula: QQ'NH, wherein

Q and Q' are the same or different and each independently represent a saturated or unsaturated hydrocarbon group which may be substituted or an aryl group (e.g. phenyl or naphthyl) which may be substituted, or Q and Q' may together form an alkylene group or an alkenylene group, both of which may be substituted with at least one $(C_1-C_3)$alkyl group and may contain a hetero atom (e.g., an oxygen atom).

The tertiary amine includes an amine compound of a formula: QQ'Q"N, wherein Q and Q' are the same as define above and Q" independently has the same meaning as Q or Q".

The saturated hydrocarbon group which may be substituted in Q, Q', Q" includes:
  a straight or branched chain $(C_1-C_{20})$alkyl group or a $(C_3-C_8)$cyclo alkyl group all of which may be substituted with a $(C_1-C_8)$alkoxy group or an aryl(e.g. phenyl, naphthyl) or a heteroaryl group (e.g. pyridine).

The unsaturated hydrocarbon group which may be substituted in Q, Q', Q" includes:
  a straight or branched chain $(C_3-C_{20})$alkenyl group such as ally, methally and 2-butenyl.

The aryl group (e.g. phenyl or naphthyl) which may be substituted in Q, Q', Q" includes an aryl group which may be substituted with at least one substituent selected from a group of an $(C_1-C_6)$alkyl and an $(C_1-C_6)$alkoxy.

Examples of the primary amine include methylamine, ethylamine, n-propylamine, isopropylamine, butylamine(n-butylamine, isobutylamine, sec-butylamine, t-butylamine), cyclohexylamine, hexylamine, octylamine, 2-ethylhexylamine, 3-(2-ethylhexyloxy)propylamine, 2-methoxyethylamine, 3-ethoxypropylamine, benzylamine, aniline, 1-naphtylamine, 2-naphtylamine or the like.

Examples of the secondary amine include dimethylamine, diethylamine, dipropylamine, diisopropylamine, dibutylamine, diisobutylamine, dicyclohexylamine di(methoxyethyl)amine, di-(allyl)amine or the like Examples of the secondary amine, formed by Q and Q', comprising an alkylene group or an alkenylene group, both of which may be substituted with at least one $(C_1-C_3)$alkyl group and may contain a hetero atom (e.g., an oxygen atom) include:
  2-pipecoline, 3-pipecoline, 4-pipecoline, piperizine, pyrrolidine and morpholine.

Examples of the tertiary amine include trimethylamine, triethylamine, tripropylamine, tributylamine, triisobutylamine, diisopropylethylamine, triallyamine, N,N-dimethylbenzylamine, N,N-dimethyl-N-1-naphthylmethylamine, N,N-diethylaniline, N-methylpiperidine, N-methylmorpholine and the like.

Examples of the secondary or tertiary amine further include a polyamine of the formula: QQ'N—Y—NQ"Q'" or QNH—Y—NHQ' or QNH—Y—NQ'Q", wherein Q,Q' and Q" independently have the same meaning as defined above and Q'" independently has the same meaning as defined for Q, Q' or Q" above and Y represents an alkylene or alkenylene hydrocarbon group having 2 to 6 carbon atoms.

Specific examples of the polyamine include N,N'-dimethylethylenediamine, N,N',N"-trimethylethylenediamine, N,N-diethyl-N'-methylethylenediamine, N,N,N'-trimethyl-1,3-propanediamine, N,N,N',N'-tetramethyl-1,3-diaminopropane, N,N,N',N'-tetramethyl-1,6-hexamethylenediamine, 2-methylpiprerazine, 2,5-dimethylpiperazine, 2,6-dimethylpiperazine, N-methylpiperazine, 1,3-di(4-piperidyl)propane, 1,5-diazabicyclo[4,3,0]non-5-ene, 1,4-diazabicyclo[2,2,2]octane and 1,8-diazabicyclo[5,4,0]undec-7-ene and further include 2-aminopyridine, 3-aminopyridine, 4-aminopyridine, 4-(N,N-dimethylamino)pyridine, 4-pyrrolidinopyridine, 4-piperidinopyridine.

Examples of the inorganic acid salt of the amine include a hydrochloride, hydrobromide, sulfate, hydrogensulfate of the corresponding amine as defined above.

Specific examples of tertiary amine hydrocloride are trimethylamine hydrochloride, triethylamine hydrochloride and the like.

Examples of the quaternary ammonium salt include triethylbenzylammonium chloride, tetramethylammonium chloride, tetramethylammonium bromide, tetraethylammonium chloride, tetraethylammonium bromide, tetrabutylammonium chloride, tetrabutylammoium bromide; and the like, respectively.

The amount of the amine or its inorganic acid salt or quaternary ammonium salt may be catalytic and is usually from 0.005 to 0.5 mol, preferably from 0.01 to 0.3 mol per mol of β-haloethylarylsulfone.

The reaction is usually conducted in an inert solvent that does not adversely affect the reaction, and the examples of the solvent include a hydrophobic organic solvent selected from an ether solvent such as diethoxymethane, ethyl ether and the like, an aromatic solvent such as benzene, toluene, xylene, chlorobenzene, dichlorobenzene and the like, a halogenated hydrocarbon solvent such as dichloromethane, 1,2-dichloroethane, chloroform, carbon tetrachloride, a mixed solvent thereof. In this reaction an aprotic polar organic solvent such as N,N-dimethylacetamide, N,N-dimethylformamide, dimethylsulfoxide or a mixed solvent thereof also may be used.

The amount of the solvent is usually from 0.5 to 50 times by weight based on the weight of β-haloethylarylsulfone.

The reaction is conducted, for example, by mixing β-haloethylarylsulfone, catalytic amount of the amine or its inorganic acid salt or quaternary ammonium salt and alkali metal carbonate or alkali metal hydrogen carbonate in a solvent. When the alkali metal carbonate or alkali metal hydrogencarbonate is used in a form of an aqueous solution, the reaction may be conducted in a two-phase system comprising a hydrophobic organic solvent and water.

The reaction temperature is usually from 0 to 150° C., and preferably from 10 to 100° C.

After completion of the reaction, water is usually added to the resulting reaction mixture, then the mixture is separated to give an aqueous phase and an organic phase of hydrophobic organic solvent containing the product, or extracted with a hydrophobic organic solvent when an aprotic polar solvent was used.

When the alkali metal carbonate or alkali metal hydrogencarbonate is used in a form of an aqueous solution in the reaction, the separation may be conducted without adding water.

After the separation, the resulted organic phase may be washed with water or an acidic aqueous solution such as diluted sulfuric acid, diluted hydrochloric acid and the like, if necessary.

Then, desired arylvinylsulfone of the formula [I] can be isolated from the resulting organic phase by a usual method, for example, by distilling off the solvent or cooling the solution Alternatively, desired arylvinylsulfone of the formula [I] may be isolated from the organic phase by using a bad solvent. For example, the organic phase may be added to a bad solvent or a bad solvent may be added to the organic phase, and crystals of the desired product are allowed to form in the mixed organic solution on standing at an ambient temperature, or the resulting mixed solution may be successively cooled, for example, to a room temperature to −50° C. to obtain the desired product, if necessary.

Examples of the bad solvent include aliphatic hydrocarbon solvent such as hexane and heptane.

The amount of the bad solvent is usually less than 100 times, preferably 0.5 to 50 times by weight based on the weight content of the desired product in the organic phase, which can be determined by a conventional analysis of the organic phase prior to the crystallization procedure.

The obtained arylvinylsulfone may be further purified by washing, recrystallization and the like, if necessary.

The examples of thus obtained arylvinylsulfone include: phenylvinylsulfone, (4-chlorophenyl)vinylsulfone, (3,4-dichlorophenyl)vinylsulfone, (4-bromophenyl) vinylsulfone, (4-fluorophenyl)vinylsulfone, (4-iodophenyl) vinylsulfone, (4-methylphenyl)vinylsulfone, (2,4-dimethylphenyl)vinylsulfone, (4-ethylphenyl)vinylsulfone, (4-i-butylphenyl)vinyl-sulfone, (4-t-butylphenyl) vinylsulfone, (4-methoxyphenyl)vinylsulfone, (3,4-dimethoxyphenyl)vinylsulfone, (4-t-butoxyphenyl) vinylsulfone, (3-aminophenyl)vinylsulfone, (3-methylaminophenol)vinylsulfone, (3-ethylaminophenyl) vinylsulfone, (3-dimethylaminophenyl)vinylsulfone, (3-diethylaminophenyl)vinylsulfone, (3-nitrophenyl) vinylsulfone and the like.

Next a description will be made to the method for producing β-haloethylarylsulfone of the formula [II] as defined above, which comprises reacting 2-arylsulfonylethanol of the formula [III] as defined above, with a chlorinating agent.

Examples of 2-arylsulfonylethanol of the formula [III] include 2-(phenylsulfonyl)ethanol, 2-(4-chlorophenylsulfonyl)ethanol, 2-(3,4-dichlorophenylsulfonyl)ethanol, 2-(4-bromophenylsulfonyl) ethanol, 2-(4-fluorophenylsulfonyl)ethanol, 2-(4-iodophenylsulfonyl)ethanol, 2-(4-methylphenylsulfonyl) ethanol, 2-(2,4-dimethylphenylsulfonyl)ethanol, 2-(4-ethylphenylsulfonyl)ethanol, 2-(4-i-butylphenylsulfonyl) ethanol, 2-(4-t-butylphenylsulfonyl)ethanol, 2-(4-methoxyphenylsulfonyl)ethanol, 2-(3,4-dimethoxyphenylsulfonyl)ethanol, 2-(4-t-butoxyphenylsulfonyl)ethanol, 2-(3-aminophenylsulfonyl) ethanol, 2-(3-methylaminophenylsulfonyl)ethanol, 2-(3-ethylaminophenylsulfonyl)ethanol, 2-(3-dimethylaminophenylsulfonyl)ethanol, 2-(3-diethylaminophenylsulfonyl)ethanol, 2-(3-nitrophenylsulfonyl)ethanol and the like.

These 2-arylsulfonylethanols can be easily produced, for example, by reacting a thiophenol with ethylene oxide or 2-chloroethanol to obtain a sulfide compound and the resulted compound is oxidized [for example, Japanese Patent Application Publication JP Hei 4-17182B, Bull. Korean Chem. Soc., 16, 670 (1995)], and the like. In addition, the substituent on the aromatic ring may be optionally introduced by a conventional method after a sulfone group is introduced, if necessary.

Examples of the chlorinating agent include thionyl chloride, phosphorus trichloride, phosphorus pentachloride, phosphorus oxychloride, and the like. Among them, thionyl chloride is preferred. The amount of the chlorinating agent is usually 1 mol, preferably 1 to 2 mols per mol of 2-arylsulfonylethanol.

The chlorinating reaction may be conducted either in a solvent or without using a solvent. When a solvent is employed in this reaction, the examples of the solvent that can be used include an inert aprotic organic solvent that does not adversely affect the reaction Such an inert solvent includes an ether solvent such as dimethoxyethane, ethyl ether and the like, an aromatic solvent such as benzene, toluene, xylene, chlorobenzene, dichlorobenzene and the like, a halogenated hydrocarbon solvent such as dichloromethane, 1,2-dichloroethane, chloroform, carbon tetrachloride and the like and a mixed solvent thereof.

The amount of the solvent to be used is usually from 0.5 to 30 times by weight based on the weight of 2-arylsulfonylethanol.

In the chlorinating reaction, an organic base may be added, if necessary, and the examples thereof include an amine such as pyridine, triethylamine and other amines as described above. Anhydrous organic bases other than aqueous solution are used in this reaction.

The amount of the organic base to be used is usually not limited and is not less than 0.001 mol to 2 mols, preferably from 0.01 to 0.5 mol per mol of the chlorinating agent.

The reaction is conducted, for example, by mixing 2-arylsulfonylethanol and a chlorinating agent, and when a solvent is used, 2-arylsulfonylethanol and a chlorinating agent may be mixed in a solvent.

When an organic base is used, the base may be added together with 2-arylsulfonylethanol and a chlorinating agent. The reaction temperature is usually from −30 to 150° C., and preferably from −10 to 100° C.

After completion of the reaction, the reaction mixture is usually subjected to a post-treatment such as dilution with water and/or extraction with an organic hydrophobic solvent or washed with water or aqueous alkali solution such as an aqueous sodium carbonate solution, an aqueous sodium hydrogencarbonate solution, aqueous potassium carbonate solution, aqueous potassium hydrogencarbonate solution and the like to remove an acidic substance resulted from the reaction prior to the next reaction to produce arylvinylsulfone of the formula [I], if necessary. Then β-haloethylarylsulfone of the formula [II] may be isolated by evaporation of the solvent used or further reacted to obtain arylvinylsulfone [I] without isolating.

According to the method of the present invention, arylvinylsulfone can be produced by a simple treatment in a good yield from industrially readily available 2-arylsulfonylethanol.

EXAMPLE

The following examples further illustrate the present invention in detail but are not to be construed to limit the scope thereof.

Example 1

(β-chloroethylsulfonyl)benzene (40.9 g, 200 mmol) was dissolved in 100 g of toluene, to this solution were added 30.7 g of 49% aqueous potassium carbonate solution (potassium carbonate 109 mmol) and 1.01 g (10 mmol) of triethylamine, and the mixture was stirred for 3 hours at from 40 to 45° C. Then, the mixture was washed with 70 g of water once, with 35 g of 5% aqueous sulfuric acid solution once and further with 35 g of water once, and the solvents were distilled off to obtain 33.1 g (yield 98.4%) of phenylvinylsulfone.

Example 2

The same reaction was conducted as in Example 1 except that 55.6 g of 20% aqueous sodium carbonate solution (sodium carbonate 105 mmol) was used instead of 49% aqueous potassium carbonate solution, to obtain 30.6 g (yield 91.0%) of phenylvinylsulfone.

Example 3

1-(β-chloroethylsulfonyl)-3-nitrobenzene (2.50 g, 10 mmol) was added to 20 g of toluene, to this solution were added 1.50 g of 49% aqueous potassium carbonate solution (potassium carbonate 5.3 mmol) and 50 mg (0.5 mmol) of triethylamine, and the mixture was stirred for 2 hours at 40° C. Then, 10 g of water was added and the mixture was separated to an organic phase and aqueous phase. This aqueous phase was extracted by chloroform, and the resulted organic phase was combined with the previous organic phase, dried over magnesium sulfate, the solvents were distilled off, to obtain 2.00 g (yield 94.3%) of (3-nitrophenyl)vinylsulfone.

Example 4

(β-chloroethylsulfonyl)benzene (4.09 g, 20 mmol) was added to 20 g of toluene, to this solution were added 3.00 g of 49% aqueous potassium carbonate solution (potassium carbonate 10.6 mmol) and 113 mg (1.0 mmol) or diisopropylethylamine, and the mixture was stirred for 4 hours at 40° C. Then, 10 g of water was added and the mixture was separated to an organic phase and aqueous phase. This aqueous phase was extracted by chloroform, and the resulted organic phase was combined with the previous organic phase, dried over magnesium sulfate, the solvents were distilled off, to obtain 2.76 g (yield 82.1%) of phenylvinylsulfone.

Example 5

The same procedure was conducted as in Example 4 except that 230 mg (1.0 mmol) of triethylbenzylammonium chloride was used instead of diisopropylethylamine, to obtain 30.4 g (yield 90.4%) of phenylvinylsulfone.

Example 6

The same procedure was conducted as in Example 4 except that 290 mg (2.0 mmol) of triisopropylamine was used instead of diisopropylethylamine, to obtain 33.3 g (yield 99.0%) of phenylvinylsulfone.

Example 7

The same procedure was conducted as in Example 4 except that 300 mg (3.0 mmol) of diisopropylamine was used instead of diisopropylethylamine, to obtain 32.7 g (yield 97.2%) of phenylvinylsulfone.

Example 8

The same procedure was conducted as in Example 4 except that 610 mg (4.0 mmol) of 1,8-diazabicyclo[5.4.0]undec-7-ene was used instead of diisopropylethylamine, to obtain 30.4 g (yield 90.4%) of phenylvinylsulfone.

Example 9

2-(phenylsulfonyl)ethanol (143.8 g, purity 96.2%, 743 mmol) was added to 71.9 g of toluene, and 30.0 g (38 mmol) of pyridine was added to the mixture. The resulting solution was heated to 60° C., then 110.5 g (929 mmol) of thionyl chloride added over 5 hours at 60 to 70° C., and the mixture was stirred for 2 hours at 70° C. Then, the mixture was diluted with 143.9 g of toluene and cooled to 45° C. Then 303.2 g of 7% sodium bicarbonate solution and 193.4 g of toluene were added, washed separated. Obtained organic layer was mixed with 303.2 g of 7% sodium bicarbonate solution and stirred and separated. 5 g of the organic layer was sampled and subjected to HPLC analysis, which revealed that (β-chloroethylsulfonyl)benzene was obtained in a yield of 98% and phenylvinylsulfone in a yield of 0.7%. (Internal Standard: methyl benzoate).

3.7 g (36 mmol) of triethylamaine was added to the obtained organic solution and the resulting solution was heated to 60° C., into which was added 202.6 g of 25% aqueous potassium carbonate over 3 hours and kept at 60° C. for 5 hours. Then the solution was cooled to room temperature and separated. Separated organic layer was washed with 57.9 g of 5% sulfuric acid twice and separated. Washed organic layer was further washed with 57.9 g of water and separated. 0.5 g of the organic layer was sampled and subjected to HPLC analysis, which revealed that phenylvinylsulfone was obtained in a yield of 100% (Internal Standard: methyl benzoate). Obtained solution was concentrated under reduced pressure to give 50% phenylvinylsulfone solution in toluene at 50° C. which was then added dropwise to 186 g of hexane under an ambient temperature and then cooled to −10° C. and kept at the same temperature for half an hour to yield crystals of phenylvinylsulfone, which was then collected by filtration. Collected crystal was washed with 250 g of hexane and dried to give 121.5 g of phenylvinylsulfone as a white crystal. (Yield: 97.9%)

What is claimed is:

1. A method for producing arylvinylsulfone represented by the general formula:

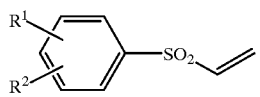

[I]

wherein, $R^1$ and $R^2$ indicate each independently a hydrogen atom, a halogen atom, a lover alkyl group, a lower alkoxy group, a nitro group, an amino group, a lower alkylamino group and a lower di(alkyl)amino group, which comprises reacting β-haloethylarylsulfone of the formula:

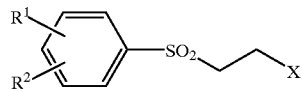

[II]

wherein, $R^1$ and $R^2$ are as defined above and X denotes a halogen atom, with an alkali metal carbonate or an alkali metal hydrogencarbonate or a mixture thereof in the presence of a catalytic amount of an amine or its inorganic acid salt or a quaternary ammonium salt.

2. The method for producing arylvinylsulfone according to claim 1, wherein the alkali metal carbonate or alkali metal hydrogencarbonate is used in a form of aqueous solution.

3. The method for producing arylvinylsulfone according to claim 1 or 2, wherein the alkali metal carbonate is potassium carbonate, sodium carbonate or a mixture thereof.

4. The method according to claim 2, wherein the amine is a secondary or tertiary amine.

5. The method according to claim 1, 2 or 4, wherein the alkali metal hydrogencarbonate is potassium hydrogencarbonate, sodium hydrogencarbonate or a mixture thereof.

6. The method according to claim 4, wherein the secondary amine is dimethylamine, diethylamine, dipropylamine, diisopropylamine, dibutylamine or diisobutylamine.

7. The method according to claim 4, wherein the tertiary amine is trimethylamine, triethylamine, tripropylamine, tributylamine, triisobutylamine, diisopropylethylamine, N,N-dimethylbenzylamine,. 1,5-diazabicyclo[4,3.0]non-5-ene or 1,8-diazabicyclo [5.4.0]undec-7-ene.

8. The method according to claim 5, wherein the inorganic acid salt of a tertiary amine is a hydrochloride of trimethylamine or a hydrochloride of triethylamine.

9. The method for producing an arylvinylsulfone according to claim 5, wherein the qauaternary ammonium salt is triethylbenzylammonium chloride, tetramethylammonium chloride, tetramethylammonium bromide, tetraethylammonium. chloride, tetraethylammonium bromide, tetrabutylammonium chloride or tetrabutylammonium bromide.

10. The method for producing arylvinylsulfone according to claim 1 or 2, wherein the amount of the secondary or tertiary amine or its inorganic acid salt or a quaternary ammonium salt is from 0.005 to 0.5 mol per mol of β-haloethylarylsulfone of the formula [II].

11. The method according to claim 1 or 2, wherein the amount of the alkali metal carbonate or alkali metal hydrogencarbonate is not less than 0.8 mol in terms of alkali metal per mol of β-haloethylarylsulfone of the formula [II].

12. The method according to claim 1 or 2, wherein the reaction is conducted at a temperature of from 0 to 150° C.

13. A method for producing β-haloethylarylsulfone of the formula [II] as defined in claim 1, which comprises reacting 2-arylsulfonylethanol of the formula:

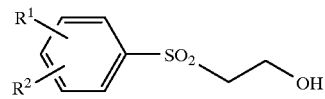

[III]

wherein, $R^1$ and $R^2$ are as defined in claim 1, with a chlorinating agent.

14. The method according to claim 13, wherein the chlorinating agent is thionyl chloride.

15. The method for producing arylvinylsulfone according to claim 13, wherein the amount of the chlorinating agent is not less than 1 mol per mol of 2-arylsulfonylethanol of the formula [III].

16. The method for producing arylvinylsulfone according to claim 13, wherein the chlorinating reaction is conducted in the presence of an organic base.

17. The method for producing arylvinylsulfone according to claim 1 or 2, wherein β-haloethylarylsulfone of the formula [I] as defined in claim 1 is obtained by a method according to any one of claims 13 to 15.

18. The method according to claim 2, wherein the reaction is conducted in a two phase system comprising water and a hydrophobic organic solvent selected from an ether, aromatic or halogenated hydrocarbon solvent.

19. The method according to claim 18, wherein separated organic phase of hydrophobic organic solvent containing arylvinylsulfone of the formula [I] after completion of the reaction is added to a bad solvent to isolate the crystals of arylvinylsulfone of the formula [I].

* * * * *